(12) United States Patent
Tamez

(10) Patent No.: US 6,189,545 B1
(45) Date of Patent: Feb. 20, 2001

(54) APPLE-SHAPED DENTAL FLOSS DISPENSER AND METHOD THEREFOR

(75) Inventor: Elias Tamez, Mabton, WA (US)

(73) Assignee: Eric Longan, Mabton, WA (US); a part interest ( * ) Notice: Under 35 U.S.C. 154(b), the term of this patent shall be extended for 0 days.

(21) Appl. No.: 09/422,226

(22) Filed: Oct. 21, 1999

Related U.S. Application Data

(63) Continuation of application No. 29/108,861, filed on Aug. 2, 1999.

(51) Int. Cl.[7] ............................. A61C 15/00; A61B 19/02
(52) U.S. Cl. .......................... 132/321; 132/323; 132/324; 132/325; D28/64; 206/63.5
(58) Field of Search ..................................... 132/321, 323, 132/324, 325, 326, 329, 327; 601/162, 164; 221/24; D28/64, 65, 66, 67, 68; 206/63.5

(56) References Cited

U.S. PATENT DOCUMENTS

| | | | |
|---|---|---|---|
| D. 311,259 | * 10/1990 | Smith | D28/64 |
| D. 367,547 | * 2/1996 | Dunn | D28/64 |
| D. 368,327 | * 3/1996 | Dunn | D28/64 |
| D. 377,998 | * 2/1997 | Dunn | D28/64 |
| D. 387,494 | * 12/1997 | Hester | D28/64 |
| D. 388,548 | * 12/1997 | Hester | D28/64 |
| D. 411,335 | * 6/1999 | Hester | D28/65 |
| 4,308,880 | * 1/1982 | Graves | 132/321 |
| 4,796,783 | * 1/1989 | Paulson | 222/80 |
| 4,903,687 | * 2/1990 | Lih-sheng | 129/66 |
| 5,076,302 | * 12/1991 | Chari | 132/325 |
| 5,076,423 | * 12/1991 | Russack | 206/63.5 |
| 5,732,722 | * 3/1998 | Mortvedt | 132/325 |

* cited by examiner

*Primary Examiner*—John J. Wilson
*Assistant Examiner*—Robyn Kieu Doan
(74) *Attorney, Agent, or Firm*—Jeffrey Weiss; Jeffrey D. Moy; Weiss & Moy, P.C.

(57) ABSTRACT

A dental floss dispenser having the external appearance of an apple. In one embodiment, the dispenser consists of two simulated apple halves, hingedly connected to one another. In another embodiment, the dispenser consists of a simulated apple half hingedly connected to a vertical backing member such as a board or wall.

9 Claims, 2 Drawing Sheets

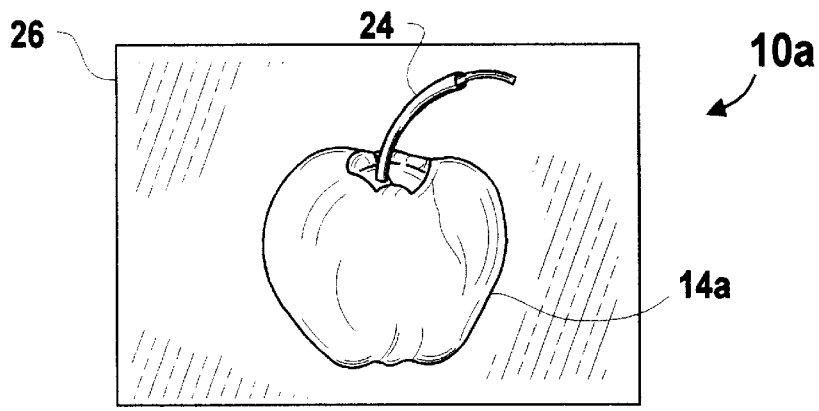
*Fig. 7*
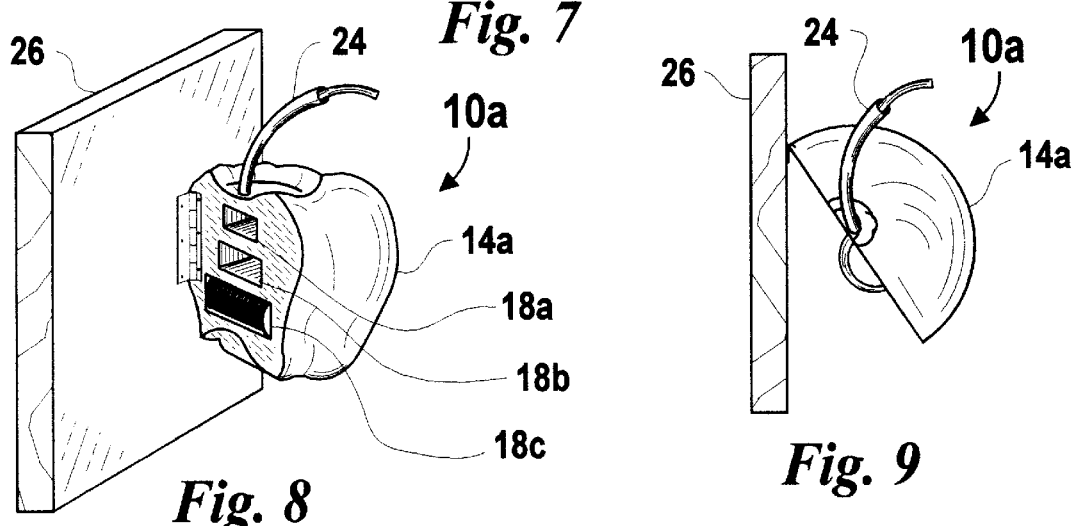
*Fig. 8*
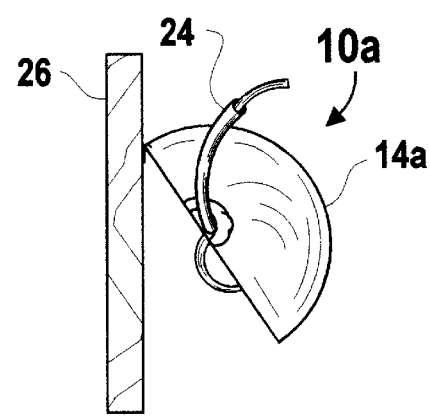
*Fig. 9*
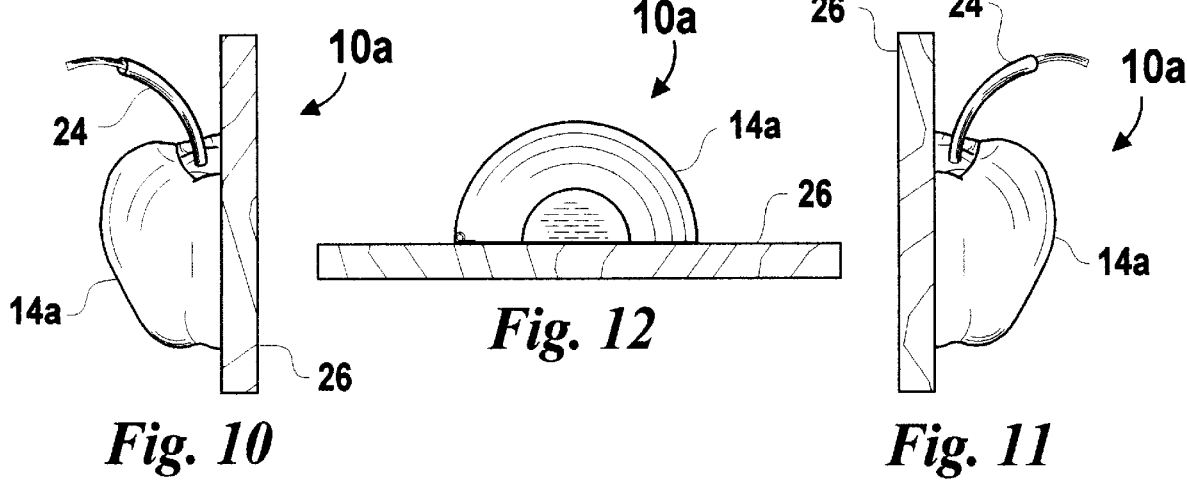
*Fig. 10*   *Fig. 12*   *Fig. 11*

APPLE-SHAPED DENTAL FLOSS DISPENSER AND METHOD THEREFOR

RELATED APPLICATION

This is a Continuation of U.S. Ser. No. 29/108,861, filed Aug. 2, 1999, in the name of the applicant of this application.

FIELD OF INVENTION

This invention relates generally to dental floss dispensing devices and methods and, more specifically, to an apple-shaped dental floss dispenser and method.

BACKGROUND OF THE INVENTION

The dental health benefits associated with the regular use of dental floss are well-known and essentially universally accepted. Nevertheless, many people do not floss regularly, for a variety of reasons. Often, people fail to floss because a floss dispenser is not readily at hand when the person is brushing his or her teeth or otherwise attending to his or her dental health needs.

Over the years, some efforts have been made to develop dental floss dispensers having greater convenience and greater aesthetic appeal, presumably in the belief that such qualities would make a person more likely to position floss in a location where it would be likely to be used. For example, U.S. Pat. No. 5,097,964 issued to Fitz discloses a dental floss dispenser in the shape of a "toothed character," wherein a dental floss spool is positioned within the character through a bottom portion thereof, and floss is passed out of the character's hand and cut at the character's teeth. While the device disclosed in Fitz in more aesthetically pleasing than non-decorative dispensers, the feature of having the floss pass outside of the character in an exposed manner makes it apparent that the "toothed character" is a floss dispenser. Moreover, a toothed character is not necessarily the type of decorative object that one commonly sees as a house decoration, particularly in rooms outside of the bathroom. For these reasons, a user may not be comfortable displaying the dispenser on a counter or other public space within the house—and particularly not in a public space outside of a bathroom. Thus, notwithstanding its aesthetic qualities, the dispenser of Fitz may also not be used as frequently as desired for good dental health, in those instances where it is concealed from view in a draw or cabinet. Further limiting the utility of the dispenser of Fitz is the fact that it is dimensioned to carry only one size of floss at any particular time, making it unsuitable for efficient use by two persons requiring different types of floss.

Therefore, a need existed to provide a floss dispenser that is aesthetically pleasing in appearance, while effectively concealing to the unsuspecting eye that it is in fact a floss dispenser. The outer configuration of the floss dispenser should, moreover, be of a type commonly seen in decorative objects displayed in a home, including in rooms other than the bathroom. The floss dispenser should further, preferably, be dimensioned to simultaneously carry more than one floss spool, so that more than one type of floss may be dispensed therethrough without the need for "reloading" the dispenser.

SUMMARY OF THE INVENTION

It is an object of the present invention to provide a dental floss dispenser that is aesthetically pleasing in appearance, while effectively concealing to the unsuspecting eye that it is in fact a floss dispenser.

It is a further object of the present invention to provide a dental floss dispenser having an outer configuration of a type commonly seen in decorative objects displayed in a home, including in rooms other than the bathroom.

It is a still further object of the present invention to provide a dental floss dispenser that is dimensioned to simultaneously carry more than one floss spool.

BRIEF DESCRIPTION OF THE PREFERRED EMBODIMENTS

In accordance with one embodiment of the present invention, a dental floss dispenser is disclosed. The dental floss dispenser comprises, in combination: a substantially apple-shaped decorative holding structure comprising first and second vertical members; wherein the first member comprises substantially one-half of an outer configuration of an apple and a first flat vertical face; wherein the second vertical member comprises a second flat vertical face; a hinge member adapted to hingedly connect the first and the second vertical members to one another so that the first and the second flat vertical faces contact each other when the first and the second vertical members are closed about the hinge member; at least one cavity dimensioned to receive a dental floss spool and located within the first flat vertical face of the first vertical member of the substantially apple-shaped decorative holding structure and positioned opposite the second flat vertical face of the second vertical member; at least one dental floss spool rotatably secured in the at least one cavity; an apple item-shaped tube located at an upper portion of the first vertical member above the cavity and dimensioned to receive therethrough a strand of dental floss; and an opening located in the first vertical face of the first vertical member and dimensioned to receive therethrough the strand of dental floss, wherein the opening leads to the apple stem-shaped tube.

In accordance with another embodiment of the present invention, a method for providing a dental floss dispenser is disclosed. The method comprises the steps of: providing a substantially apple-shaped decorative holding structure comprising first and second vertical members; wherein the first member comprises substantially one-half of an outer configuration of an apple and a first flat vertical face; wherein the second vertical member comprises a second flat vertical face; providing a hinge member adapted to hingedly connect the first and the second vertical members to one another so that the first and the second flat vertical faces contact each other when the first and the second vertical members are closed about the hinge member; providing at least one cavity dimensioned to receive a dental floss spool and located within the first flat vertical face of the first vertical member of the substantially apple-shaped decorative holding structure and positioned opposite the second flat vertical face of the second vertical member; rotatably securing at least one dental floss spool in the at least one cavity; providing an apple stem-shaped tube located at an upper portion of the first vertical member above the cavity and dimensioned to receive therethrough a strand of dental floss; and providing an opening located in the first vertical face of the first vertical member and dimensioned to receive therethrough the strand of dental floss, wherein the opening leads to the apple stem-shaped tube.

The foregoing and other objects, features, and advantages of the invention will be apparent from the following, more particular, description of the preferred embodiments of the invention, as illustrated in the accompanying drawings.

BRIEF DESCRIPTION OF THE DRAWINGS

FIG. 7 is a side elevational view of the dental floss dispenser depicting another embodiment showing a half apple configuration mounted on a backing member.

FIG. 8 is a side perspective view of the dental floss dispenser of FIG. 7 showing a hinged connection to the backing member and the dental floss spool being used plus multiple dental floss compartments.

FIG. 9 is a top view of the dispenser shown in FIG. 8.

FIG. 10 is a right side elevational view of the dispenser shown in FIG. 7.

FIG. 11 is a left side elevational view of the dispenser shown in FIG. 7.

FIG. 12 is a bottom view of the dispenser shown in FIG. 7.

DETAILED DESCRIPTION OF THE PREFERRED EMBODIMENTS

Figure 1:
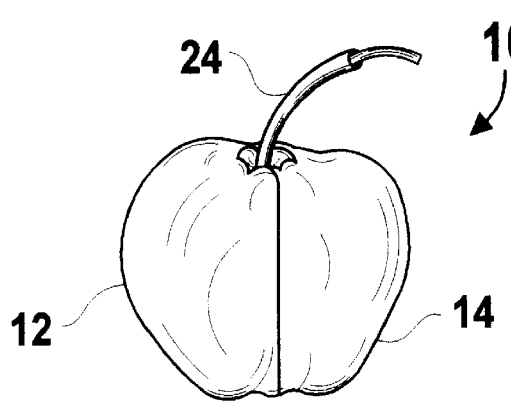
FIG. 1 is a side elevational view of one embodiment of the dental floss dispenser of the present invention.
Figure 2:
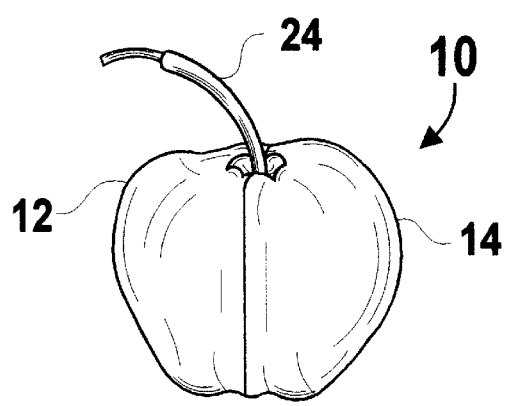
FIG. 2 is the other side elevational view of the dental floss dispenser of FIG. 1.

Referring to FIGS. 1–5, reference number 10 refers generally to one embodiment of the dental floss dispenser 10 (hereinafter "dispenser 10") of the present invention. The dispenser 10 comprises a first half 12 and a second half 14, which halves 12 and 14 each have the external configuration of one vertical half of an apple. The halves 12 and 14 are hingedly connected with an internal hinge 16 (see FIG. 4). The internal hinge 16, the positioning of which is shown in broken lines in FIGS. 2, 4 and 5, should preferably not be visible from outside of the dispenser 10 when it is in the closed position. Such a configuration enhances the apple appearance of the dispenser 10, and may lead a casual observer of the closed dispenser 10 to believe that it is in fact a real apple.

Figure 3:
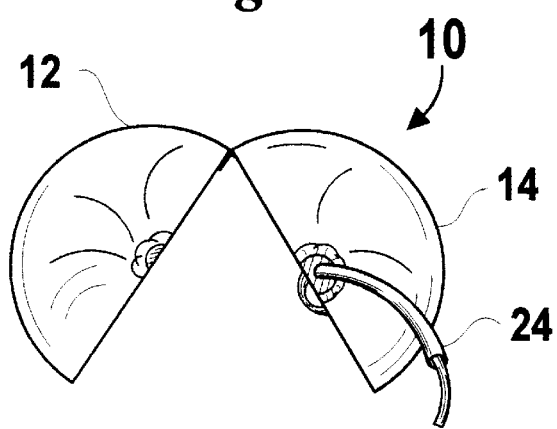
FIG. 3 is a top view of the dental floss dispenser shown in an opened configuration about the internal hinge.
Figure 4:
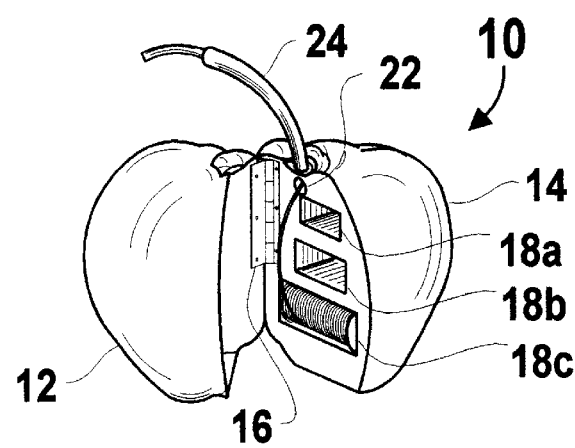
FIG. 4 is a perspective view showing the interior of the dental floss dispenser illustrating the use of at least one dental floss spool and multiple compartments to contain other sizes of dental floss spools.
Figure 5:
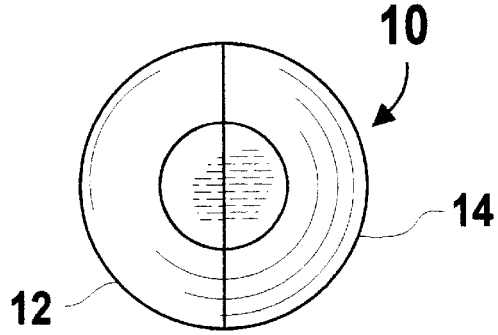
FIG. 5 is a bottom view of the dental floss dispenser of FIG. 1.
Figure 6:
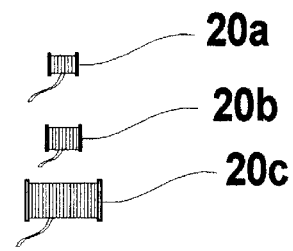
FIG. 6 is a side elevational view of multiple sizes of dental floss spools for use in the multiple compartments shown in FIG. 4.

Referring specifically to FIGS. 3 and 4, halves 12 and 14 are distinguished from one another in two principle ways. Thus, the second half 14 preferably contains three recessed floss compartment 18a, b and c of different dimension, for receiving corresponding differently sized floss spools 20a, b and c (see FIG. 6). (Reference number 18, without a letter suffix, is used herein to refer to a generic compartment 18.) In this manner, the dispenser 10 can, for example, simultaneously carry floss spools 20 having different gauge floss. While the individual compartments 20a, b and c may be of different dimensions as shown in FIG. 4, they may also be equivalently sized without departing from the spirit or scope of the present invention. (Reference number 20, without a letter suffix, is used herein to refer to a generic floss spool 20.) Moreover, the second half 14 may also be configured to include only two compartments 18, instead of three components 18 as shown in FIG. 4, without departing from the spirit of scope of the present invention.

Located above the compartment 18, as shown in FIG. 4, is an internal opening 22. The internal opening 22 leads to the hollow, tube-like stem 24 (hereinafter "stem 24"), so that floss from a spool 20 located within a compartment 18 may enter the internal opening 22 and, as shown in FIGS. 1–4, exit through the end of the stem 24. Although the floss may extend slightly beyond the end of the stem 24, it will appear to a casual observer to simply be part of the stem 24, and will not be readily identifiable as floss. This is particular so inasmuch as apples are commonly used as decorative objects in households, including in kitchens and bathrooms. (Indeed, in a kitchen setting, the apple configuration may lead the dispenser 10 to be confused with a real apple.) Without departing from the spirit or scope of the invention, it would be possible to simply eliminate the stem 24, so that the floss extending through the internal opening 22 would itself have the superficial appearance of an apple stem. Alternatively, in the event of the removal of the stem 24, the floss could be deployed through another opening in another portion of the apple, as desired.

While the dispenser 10 preferably comprises halves 12 and 14, it would be possible, without departing from the spirit or scope of the invention, to make the dispenser 10 essentially one-piece, with a compartment 18 located therein and accessible through a bottom portion of the dispenser 10.

Referring now to FIGS. 7–12, reference number 10a refers generally to another embodiment of the dental floss dispenser (hereinafter "dispenser 10a") of the present invention. The dispenser 10a comprises an apple half 14a that is identical, in all material respects, to the second half 14 described above, the description of which is incorporated herein by reference. Thus, with respect to the individual features of the apple half 14a, the same reference used above with respect to the second half 14 are used in FIGS. 7–11 to identify the corresponding features.

The dispenser 10a is distinguished from the dispenser 10 through the use of a backing member 26, hingedly connected to the apple half 14a, to replace the first half 12 of the dispenser 10. The backing member 26 can be any vertical surface, including without limitation a wall, a cabinet, a board, etc. Thus, for example, the dispenser 10a can comprise a backing member 26 which is a board, which dispenser 10a may then be hung in an attractive location. Alternatively, the backing member 26 may for example be a wall or cabinet in the bathroom or other room where the dispenser 10a is to be used, so that it is essentially permanently positioned in a proper place.

While the invention has been particularly shown and described with reference to preferred embodiments thereof, it will be understood by those skilled in the art that the foregoing and other changes in form and details may be made therein without departing from the spirit and scope of the invention.

I claim:

1. A dental floss dispenser comprising:
    a substantially apple-shaped decorative holding structure comprising first and second vertical members;
    wherein said first member comprises substantially one-half of an outer configuration of an apple and a first flat vertical face;
    wherein said second vertical member comprises a second flat vertical face;
    a hinge member adapted to hingedly connect said first and said second vertical members to one another so that said first and said second flat vertical faces contact each other when said first and said second vertical members are closed about said hinge member;
    at least one cavity dimensioned to receive a dental floss spool and located within said first flat vertical face of said first vertical member of said substantially apple-shaped decorative holding structure and positioned opposite said second flat vertical face of said second vertical member;

at least one dental floss spool rotatably secured in said at least one cavity;

an apple stem-shaped tube located at an upper portion of said first vertical member above said cavity and dimensioned to receive therethrough a strand of dental floss; and an opening located in said first vertical face of said first vertical member and dimensioned to receive therethrough said strand of dental floss, wherein said opening leads to said apple stem-shaped tube.

2. The dental floss dispenser of claim 1, wherein in said second vertical member comprises substantially one-half of an outer configuration of an apple and said second flat vertical face.

3. The dental floss dispenser of claim 1, wherein said second vertical member comprises at least one of a board, a wall, and a cabinet.

4. The dental floss dispenser of claim 1, comprising three cavities dimensioned to receive a dental floss spool and located within said first flat vertical face of said first vertical half of said apple-shaped decorative holding structure and positioned opposite said second flat vertical face of said second vertical half.

5. A dental floss dispenser comprising;

a substantially apple-shaped decorative holding structure comprising a backing member and a half-apple shaped member hingedly connected along one vertical portion of said half-apple shaped member to said backing member;

at least one cavity dimensioned to receive a dental floss spool and located within said half-apple shaped member of said substantially apple-shaped decorative holding structure;

at least one dental floss spool rotatably secured in said at least one cavity; and an opening located in said half-apple shaped member of said substantially apple-shaped decorative holding structure and dimensioned to receive therethrough a strand of dental floss from said dental floss spool.

6. A method for providing a dental floss dispenser comprising the steps of:

providing a substantially apple-shaped decorative holding structure comprising first and second vertical members;

wherein said first member comprises substantially one-half of an outer configuration of an apple and a first flat vertical face;

wherein said second vertical member comprises a second flat vertical face;

providing a hinge member adapted to hingedly connect said first and said second vertical members to one another so that said first and said second flat vertical faces contact each other when said first and said second vertical members are closed about said hinge members;

providing at least one cavity dimensioned to receive a dental floss spool and located within said first flat vertical face of said first vertical member of said substantially apple-shaped decorative holding structure and positioned opposite said second flat vertical face of said second vertical member;

rotatably securing at least one dental floss spool in said at least one cavity;

providing an apple stem-shaped tube located at an upper portion of said first vertical member above said cavity and dimensioned to receive therethrough a strand of dental floss; and providing an opening located in said first vertical face of said first vertical member and dimensioned to receive therethrough said strand of dental floss, wherein said opening leads to said apple stem-shaped tube.

7. The method of claim 6, wherein said second vertical member comprises substantially one-half of an outer configuration of an apple and said second flat vertical face.

8. The method of claim 6, wherein said second vertical member comprises at least one of a board, a wall, and a cabinet.

9. The method of claim 6, further comprising the step of providing three cavities dimensioned to receive a dental floss spool and located within said first flat vertical face of said first vertical half of said apple-shaped decorative holding structure and positioned opposite said second flat vertical face of said second vertical half.

* * * * *